(12) United States Patent
Monsalve Cordova

(10) Patent No.: US 10,588,468 B2
(45) Date of Patent: Mar. 17, 2020

(54) HAND PROTECTION COVER DISPENSER

(71) Applicant: Cristalino Transparente SL, Madrid (ES)

(72) Inventor: Juan Monsalve Cordova, Madrid (ES)

(73) Assignee: CRISTALINO TRANSPARENTE S.L., Madrid (ES)

( * ) Notice: Subject to any disclaimer, the term of this patent is extended or adjusted under 35 U.S.C. 154(b) by 0 days.

(21) Appl. No.: 16/437,899

(22) Filed: Jun. 11, 2019

(65) Prior Publication Data

US 2019/0387932 A1    Dec. 26, 2019

(51) Int. Cl.
*A47K 10/32* (2006.01)
*A47K 10/42* (2006.01)

(52) U.S. Cl.
CPC ............ *A47K 10/32* (2013.01); *A47K 10/426* (2013.01); *A47K 2010/3233* (2013.01)

(58) Field of Classification Search
CPC .......... A47K 10/426; A47K 2010/3233; A47K 10/32; A47K 17/003
See application file for complete search history.

(56) References Cited

U.S. PATENT DOCUMENTS

| | | | |
|---|---|---|---|
| 4,724,974 A * | 2/1988 | Marqua | A47F 1/126 206/252 |
| 4,993,589 A * | 2/1991 | McLaughlin | B65D 83/0817 221/197 |
| 5,088,620 A * | 2/1992 | Kelliher | A47F 1/06 221/59 |
| 5,816,440 A * | 10/1998 | Shields | B65D 83/0805 221/45 |
| 5,878,909 A * | 3/1999 | Rogow | A61B 42/50 221/289 |
| 5,921,434 A * | 7/1999 | Hollander | A61B 42/40 221/34 |
| 5,987,645 A * | 11/1999 | Teaster | A41D 19/0068 15/227 |
| 6,375,034 B1 * | 4/2002 | Corbett | A47G 25/904 221/30 |
| 10,478,001 B2 * | 11/2019 | Ivakhnyuk | A41D 19/0082 |
| 2004/0155051 A1 * | 8/2004 | Magid | B65D 83/12 221/59 |
| 2007/0034639 A1 * | 2/2007 | Zeiron | A47K 10/427 221/47 |
| 2007/0215635 A1 * | 9/2007 | Tramontina | A61B 50/10 221/270 |

(Continued)

*Primary Examiner* — Gene O Crawford
*Assistant Examiner* — Ayodeji T Ojofeitimi

(57) ABSTRACT

The invention discloses a hand protection cover dispenser (1) comprising: a box (2) comprising a front side (21) having an open upper portion, an upper side (22) having an upper front portion, and a spring (3); and a pile of covers (4) housed inside the box (2) and biased frontwards by the spring (3), where each cover (4) comprises a rectangular back sheet (41) having the size of the front side (21) and a front sheet (42) having a size smaller than the open upper portion of the front side (21) and being joined to lateral and upper edges of the back sheet (41) only at its lateral and upper edges. A user may introduce the hand between the back sheet (41) and the front sheet (42) by displacing it upwards under a lower edge of the front sheet (42) and extract said cover (4) by displacing the hand upwards.

6 Claims, 1 Drawing Sheet

(56) References Cited

U.S. PATENT DOCUMENTS

| | | | |
|---|---|---|---|
| 2009/0200329 A1* | 8/2009 | Balkin | A47K 10/32 221/45 |
| 2011/0186589 A1* | 8/2011 | Lee | B65D 83/00 221/36 |
| 2012/0259455 A1* | 10/2012 | Balkin | A47K 10/32 700/232 |
| 2013/0037562 A1* | 2/2013 | Close | A47F 1/126 221/279 |
| 2016/0152403 A1* | 6/2016 | Ray | B65D 83/0894 221/1 |

* cited by examiner

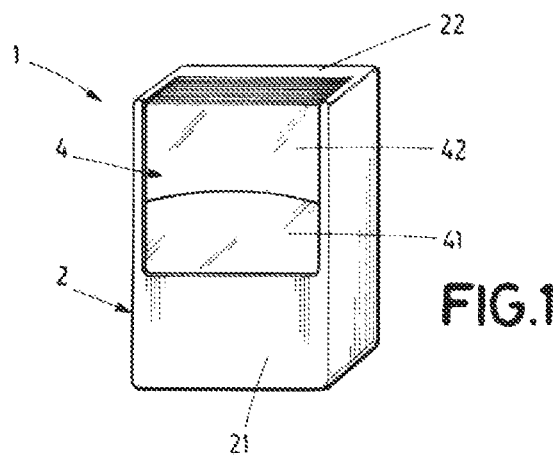
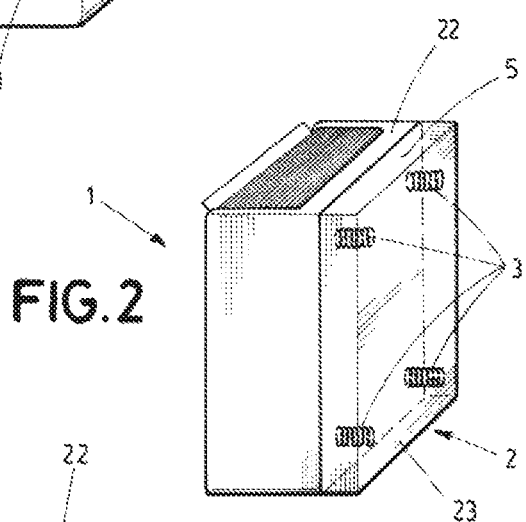
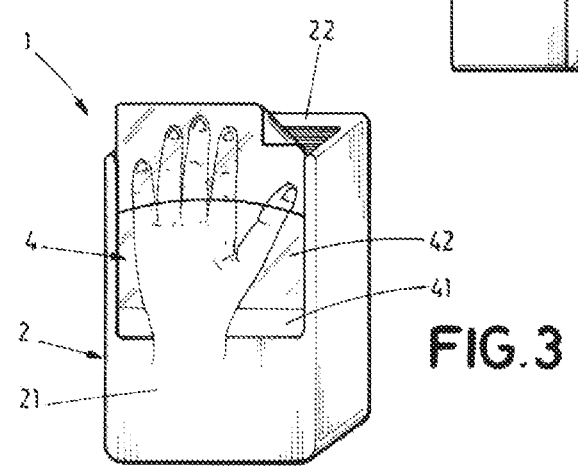

HAND PROTECTION COVER DISPENSER

OBJECT OF THE INVENTION

The object of the present invention is a new dispenser of hand covers, in the form of gloves, allowing for the user to extract each cover without touching any additional object.

BACKGROUND OF THE INVENTION

Nowadays, there are several situations where a person must use a hand protection sheath with the purpose of avoiding touching certain objects. This situation occurs, for example, in medical environments where the transmission of germs possibly present on the hands of a medical professional must be avoided. It is also common in supermarkets and grocery stores for preventing a user from touching with his/her hand a fruit or vegetable that he/she finally does not buy.

In order to solve this problem, several hand protection cover dispensers, such as globes or hand bags, are known. These dispensers are designed for allowing the user first to extract the gloves or bags one by one and, subsequently, the user puts them on.

A first exemplary configuration of a known dispenser is formed as a box housing a pile of gloves or bags and having a large enough hole for the user to introduce his/her hands to extract a glove. Once the glove or bag is extracted, the user puts it on and, subsequently, he/she repeats these steps for the second glove or bag if necessary. Document US2016051330 discloses an exemplary embodiment of this kind of devices.

A second exemplary configuration of a known dispenser is based on a roller around which a continuous web of gloves or bags separated by weakened lines, e.g. by micro-perforations, is provided. The user pulls the roller for unrolling a first glove or bag, then pulls said glove or bag for separating it from the web, and finally he/she puts it on. These dispensers a currently commonly seen in supermarkets.

Both types of dispensers have a drawback in that the user necessarily touches a plurality of surfaces before putting the glove or bag on. The user touches the dispenser itself for extracting the glove or bag, then uses both hands for putting the glove or bag on in the first hand, and lastly uses the already protected hand for putting the glove or bag on in the second hand. This manipulation increases the chance of germ transmission from the dispenser, the hands, or other surfaces near the gloves themselves.

DESCRIPTION OF THE INVENTION

The present invention solves the above drawback by means of a hand protection cover dispenser designed such that the user needs not manipulate the covers when putting them on, but he/she can introduce the hands therein during the extraction step itself. The need for the user or the cover to touch possibly contaminated surfaces is thus prevented. This new dispenser is also useful for dispensing covers made of an absorbent material, such as absorbent paper, thus allowing a person to dry his/her hands in a public toilet without the need to touch anything else but the absorbent cover.

The dispenser of the present invention mainly comprises a storage box where a pile of particularly designed hand protection covers are stored. Now, each of these elements is disclosed in detail.

a) Storage Box

The storage box is mainly parallelepipedal and, in particular, comprises a front side having an open upper portion and an upper side having an open front portion. As disclosed in detail further on in the present document, the front side having the open upper portion allows the user to introduce his/her hand in the hand protection cover, and the upper side having the open front portion allows the user to extract the cover by means of an upward movement of the hand. The other faces of the storage box will normally be closed, although the presence of holes of ornamental type or for other auxiliary uses such as facilitating the assembly and disassembly of the box or the recharging of the manual protection covers is not ruled out. The box further comprises at least a horizontal spring abutted on an inner surface of the back side of the box. A single spring or several springs may be provided, for example four, near the corners of the back side of the box for biasing continuously the pile of hand protection covers towards the front side of the box. Accordingly, it is ensured that the first hand protection cover located at the most external position abuts against the front side of the box.

As to materials, the storage box may in principle be made of any material, although plastic or metal are preferably used.

b) Cover Pile

The cover pile is a pile of hand protection covers housed inside the storage box such that they are biased frontwards by the spring. The covers have a particular design comprising an essentially rectangular back sheet having the side of the front side of the box and a front sheet having a smaller size that the open upper portion of the front side, and being joined to respective lateral and upper edges of the back sheet only at its lateral and upper edges. Thus, a pocket is formed between the back sheet and the front sheet preferably sized for essentially covering at least half the fingers between the index finger and the little finger and part of the thumb of a user.

The covers may be made of any suitable material, such as paper, plastic, latex, and the like. The material is chosen according to the user of the dispenser.

Thanks to this configuration, a user may introduce the hand in the pocket between the back sheet and the front sheet of a cover by displacing the hand upwards from under a lower edge of the front sheet. Once the hand is inside, the user can extract said cover by displacing the hand further upwards until the cover exits through the open upper portion of the upper side of the box. Therefore, the user needs not touch any surface in order to put the manual protection cover on, since the method for putting said cover on is an integral part of the method for extracting said cover from the storage box.

As to the size, the size of the storage box is similar to the size of currently known napkin dispensers, e.g. between 20-30 cm high and between 10-20 cm wide and depth. A front side having about 25 cm×15 cm, for example, has enough surface for the user to introduce a hand inside the pocket of the first hand protection cover in a simple way.

On the other hand, the open upper portion of the front side of the storage box must have a size allowing for a large enough portion of the first cover of the pile to be visible for the user to introduce his/her hand inside the pocket under the front sheet of said cover. For example, in a preferred embodiment of the invention, the open upper portion of the front side of the storage box has a size at least half the size of said front side. Further, the open front portion of the upper side of the storage box may have a size of at least two thirds of the size of said upper side.

Finally, the size of the front sheet of the cover is at least a third of the size of the back sheet. Thus, given the size of the whole cover, it is ensured that the pocket formed between the back sheet and the front sheet is deep enough for the user to introduce at least half the index to little finger and part of the thumb of the user.

BRIEF DESCRIPTION OF THE DRAWINGS

FIG. 1 shows a perspective view of a dispenser according to an example of the present invention.

FIG. 2 shows another perspective view of the exemplary dispenser according to the invention shown in FIG. 1.

FIG. 3 shows a perspective view of the process for extracting a hand cover using the dispenser of the present invention shown in FIG. 1.

PREFERRED EMBODIMENT OF THE INVENTION

FIGS. 2 and 3 show two perspective views of the dispenser (1) of the present invention where the component parts are shown.

The dispenser (1) is formed by a storage box (2) having an essentially parallelepiped shape formed by six walls or sides, particularly a lower side, lateral sides, a front side (21), an upper side (22) and a back side (23). All sides except for the front side (21) and the upper side (22) are closed, that is, lack openings or orifices communicating the inside of the box (2) with the outside. Inside the box (2) a pile of hand protection covers (4) having a size approximately equal to the size of the box (2) are housed, such that the pile of covers (4) fits perfectly inside the box (2) as in some currently known napkin dispensers.

The front side (21) of the box has an open upper portion of approximately two thirds of its surface. The open upper portion covers almost completely the upper two thirds of the front side (21) except for the narrow vertical bands located at the sides adjacent the edges of said front side (21), whose purpose is to contain the pile of covers (4) preventing them from exiting the box (2). Therefore, through the open upper portion of the front side (21) approximately the two upper thirds of the first cover (4) are accessible. The size of the upper portion is about 15 cm×15 cm, enough for easily covering approximately half the size of a user during the process for extracting the covers (4), which is disclosed in detail further down in the present document. On the other hand, the upper side (22) has an open front portion also covering about two thirds of the surface of said upper side (22). The edges of part of the pile of covers (4) are visible through the open upper portion of the upper side (21).

FIG. 2 also shows four springs (3) provided near the corners and abutting against the inner surface of the back side (23). These springs (3) are coupled to a plate (5) which is parallel to the back side (23), thus pushing said plate (5) in a direction opposite said back side (23). Thus, the plate (5) at all times biases the pile of covers (4) towards the front, causing the first cover (4) to always abut against the inner surface of the front side (21) of the box (2).

As disclosed, the pile (4) of covers is housed inside the box (2) such that a first cover (4) is accessible through the open upper portion of the front side (21). Further, each cover (4) is formed by a back sheet (41) and a front sheet (42) joined at the upper and lateral edges of the front sheet (42). Furthermore, the surface of the front sheet (42) is noticeably lower than the surface of the back sheet (41), such that a pocket is formed between them at the upper portion of the cover (4) and whose opening is oriented downwards. The size of the front sheet (42) is approximately one third of the total size of the cover (4), such that the cover (4) opening lies at a position that is accessible through the open upper portion of the front side (21).

As shown in FIG. 3, in order to extract a cover (4) the user needs only to introduce an end portion of his/her hand inside the pocket formed between the back sheet (41) and the front sheet (42), particularly half his/her fingers from the index finger to the small finger and part of his/her thumb. By pushing upwards, the hand slides to the end of the pockets, which coincides with the joint line between the upper edges of the back sheet (41) and the front sheet (42). Once there, the user may continue displacing his/her hand upwards until it exits the frontmost part of the front opening in the upper side (22). The user has already put the cover (4) on, and therefore no further manipulation is necessary. The cover (4) can be user for several tasks, such as e.g. picking up fresh products at a supermarket or drying the hands at a public toilet.

The invention claimed is:

1. Hand protection cover dispenser (1), characterized by comprising:
    an essentially parallelepiped storage box (2) comprising a front side (21) having an open upper portion, an upper side (22) having an upper front portion, and at least a horizontal spring (3) abutting an inner surface of a back side (23) of the box (2); and
    a pile of hand protection covers (4) housed inside the storage box (2) such that they are biased frontwards by the spring (3), where each cover (4) comprises an essentially rectangular back sheet (41) having the size of the front side (21) of the box (2) and a front sheet (42) having a size smaller than that of the open upper portion of the front side (21) and being joined to the lateral and upper edges of the back sheet (41) only at its lateral and upper edges,
    such that the user may introduce the hand in a pocket between the back sheet (41) and the front sheet (42) of a cover by displacing it upwards under a lower edge of the front sheet (42) and extract said cover (4) by displacing the hand further upwards until it exits through the open front portion of the upper side (22) of the box (2).

2. The dispenser (1) according to claim 1, wherein the open upper portion of the front side (21) of the storage box (2) has a size smaller than at least half the size of said front side (21).

3. The dispenser (1) according to claim 1, where the open front portion of the upper side (22) of the storage box (2) has a size of at least two thirds of the size of said upper side (22).

4. The dispenser (1) according to claim 1, where the storage box (2) is made of plastic or metal.

5. The dispenser (1) according to claim 1, where the size of the front sheet (42) of the cover (4) is at least one third of the size of the back sheet (41).

6. The dispenser (1) according to claim 1, where the covers (4) are made of paper, plastic, or latex.

* * * * *